(12) United States Patent
Ross

(10) Patent No.: US 8,057,819 B2
(45) Date of Patent: *Nov. 15, 2011

(54) STABILITY ADDITIVES FOR DRY DHA DOSAGE FORMS

(75) Inventor: Neil Ross, Weston, FL (US)

(73) Assignee: Avema Pharma Solutions, division of PL Development, Westbury, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/053,659

(22) Filed: Mar. 22, 2011

(65) Prior Publication Data

US 2011/0165233 A1 Jul. 7, 2011

Related U.S. Application Data

(63) Continuation of application No. 12/766,396, filed on Apr. 23, 2010.

(60) Provisional application No. 61/173,322, filed on Apr. 28, 2009, provisional application No. 61/173,317, filed on Apr. 28, 2009, provisional application No. 61/174,553, filed on May 1, 2009.

(51) Int. Cl.
*A61K 9/48* (2006.01)

(52) U.S. Cl. ...................................................... 424/452

(58) Field of Classification Search .................. None
See application file for complete search history.

(56) References Cited

U.S. PATENT DOCUMENTS

| 6,964,969 | B2 * | 11/2005 | McCleary | 514/283 |
|---|---|---|---|---|
| 7,704,542 | B2 * | 4/2010 | Bydlon et al. | 426/648 |
| 7,887,847 | B2 * | 2/2011 | Paul, Jr. | 424/638 |
| 2005/0249821 | A1 | 11/2005 | Paul, Jr. | |
| 2010/0047363 | A1 * | 2/2010 | Wigneswaran | 424/638 |

FOREIGN PATENT DOCUMENTS

| WO | 2008146016 | 12/2008 |
|---|---|---|
| WO | WO 2008146016 A2 * | 12/2008 |

* cited by examiner

*Primary Examiner* — Johann Richter
*Assistant Examiner* — Thor Nielsen
(74) *Attorney, Agent, or Firm* — Arnall Golden Gregory LLP; Clark G. Sullivan

(57) ABSTRACT

The use of additives to stabilize DHA when compressed into tablets, or filled as a powder into capsules, for oral administration.

6 Claims, No Drawings

STABILITY ADDITIVES FOR DRY DHA DOSAGE FORMS

This application is a continuation of U.S. patent application Ser. No. 12/766,396, filed Apr. 23, 2010 (pending), which claims the benefit of U.S. Provisional Application No. 61/173,322, filed Apr. 28, 2009, U.S. Provisional Application No. 61/173,317, filed Apr. 28, 2009, and U.S. Provisional Application No. 61/174,553, filed May 1, 2009, all four applications are herein incorporated by reference in their entirety.

FIELD OF THE INVENTION

The present invention relates to dry oral dosage forms, especially tablets and powder filled capsules, that contain docosahexaenoic acid (DHA) in large proportion. The invention further relates to excipients that stabilize the DHA in such dosage forms, especially elemental iron, chelated copper, chelated magnesium, calcium ascorbate, calcium carbonate or silicon dioxide.

BACKGROUND OF THE INVENTION

Docosahexaenoic acid, or DHA, is a molecule of intense commercial interest of late due to emerging knowledge of its benefits in the treatment and prevention of cardiovascular and neurologic conditions, and the nutritional support and well-being of mothers and developing fetuses, among other health benefits. DHA is typically sold in bulk as an oil mixture that contains other polyunsaturated fatty acids, such as eicosapentaenoic acid (EPA), although commercial sources of purified DHA, which have nominal amounts of EPA, have recently emerged.

The molecule has historically been derived from fish oil, but more recently algal oils have been isolated that are highly enriched in omega-3 fatty acids. In the case of certain fermentatively produced algae rich in omega-3 fatty acids (e.g., *Crypthecodinium cohnii* and *Schizochytrium* sp.), the process has been scaled up and commercialized. This process involves growing the algae, stressing the organisms to induce the production of an oil, harvesting and drying the algae, extracting the oil with an organic solvent, and purifying the oil using processes well known in the art for vegetable oil processing.

The DHA-enriched oils, whether derived from fish or algae, are not as stable as other vegetable oils such as corn oil, soybean oil, canola oil, palm oil, etc., because the DHA and other fatty acids are polyunsaturated and inherently susceptible to oxidative breakdown. Various attempts have been made to stabilize fish oils through the use of lipophilic antioxidants such as vitamin B, or by setting up a physical barrier between the fish oil and the food product matrix using encapsulation or coating.

Fully or partially refined marine oil has also been treated with silica and stabilized by incorporating a mixture of lecithin, ascorbyl palmitate, and alpha-tocopherol. See U.S. Pat. No. 5,855,944. Hamilton et al., J. Am. Oil Chem. Soc. (JAOCS) 75 (7), 813-822 (1998), disclose a ternary additive mixture (2% tocopherol, 0.1% ascorbyl palmitate, 0.5% lecithin) to prevent autoxidation of fish oils.

EP 340 635 describes a process of treating fish oils to increase their stability containing EPA and DHA by vacuum steam distillation under mild conditions to reduce low temperature boiling and less polar volatile flavor compounds, and subsequently contacting said oil with an adsorbent, e.g., silica gel, to reduce high temperature boiling and more polar volatile flavor compounds. The document also describes the combination of the purified oil with a rosemary extract antioxidant. US 2003/161918 A1 describes the preparation and stabilization of food-grade fish oils by treating a fish oil with silica, submitting it to a 2 hours batch vacuum steam deodorization in the presence of rosemary or sage extract and, if desired, adding ascorbyl palmitate and mixed tocopherol.

These methods, while successful, have been predominantly used to stabilize oils. To the inventors' knowledge, very little if any work has been done to stabilize polyunsaturated fatty acids, particularly DHA, when present in a dry admixture such as a tablet or powder-filled capsule. This may be because bulk DHA is practically always supplied in oil form in combination with other fatty acids, and practically always processed into liquid-filled gel-caps for eventual use by the consumer. While spray dry and encapsulation methods exist for manufacturing powdered forms of the molecule, to the inventors' knowledge, none of these powdered forms of DHA has been successfully processed, on a commercial scale, into a stable tablet or powder-filled capsule dosage form.

Various patents report having made tablets that contain polyunsaturated fatty acids. For example, U.S. Pat. No. 5,843,919 to Burger describes mixtures of glucosamine and EPA, and tablets that contain such mixtures. The document does not disclose any formulations for such tablets, and does not describe any methods for improving the stability of such tablets.

EP 342795 A2 to Taiyo describes compositions for improving cerebral function which contain DHA. Tablets are mentioned as a possible dosage form, without giving any specific formulation or any consideration to molecular stability. No consideration is given to tableting or powder-filled capsules where the fatty acid component is in the form of an oil.

WO 88/02221 by Kabivitrum describes an EPA/DHA granulate comprising an oil-powder mixture containing 2-75% vegetable oil and/or marine oil containing essential fatty acids selected from gamma linolenic acid (GLA), EPA and/or DHA and/or other marine oils and a water-soluble carrier, in combination with a solid pulverulent filler and a binder. The reference also states that tablets can be made from said granulate, and gives various excipients for use in making such tablets, including various conventional fillers, binders and additives such as vitamins and minerals. The document states that alpha tocopherol and ascorbyl palmitate can be added to the oil for protection against oxidation, but otherwise does not give meaningful consideration to the stability of the tablets or powder filled capsules or how to improve the stability.

U.S. Pat. No. 4,831,022 to Hijiya describes EPA inclusion complexes with gamma cyclodextrins with up to 47.6% EPA in the solid prepared. No consideration is given to tableting or the preparation of powder-filled capsules where the fatty acid component is in the form of an oil, or to the stability of such tablets or powder-filled capsules.

WO 2008/146016 by Campbell describes complexes of fatty acid esters and cyclodextrins that can be compressed into tablets with reportedly high concentrations of the fatty acid compound. The document reports that the complexes can be mixed with various excipients prior to compression into a tablet, including microcrystalline cellulose, stearic acid and colloidal silica. The document also reports that various drugs, vitamins and minerals can be mixed into the tablet, including simvastatin, vitamin C, calcium carbonate, folic acid, vitamin D3, vitamin K, and vitamin E. The document does not report any stability data for the various combinations, and uses mixtures of omega-3 fatty acids in the tablets rather than purified DHA.

OBJECTS OF THE INVENTION

Methods of producing tablets and powder-filled capsules that contain DHA have until now been unsatisfactory on a commercial scale. What is needed is a technology for making such tablets and capsules that can be reliably reproduced to yield tablets and capsules that contain therapeutically significant proportions of DHA, in which the DHA is stable against oxidative and other degradation. Ideally, the technology would be robust enough to allow for the integration of other nutritional ingredients into the tablet or capsule, even ingredients that might otherwise destabilize the DHA, so that multi-vitamin tablets and capsules may be prepared that contain DHA.

SUMMARY OF THE INVENTION

It has unexpectedly discovered that various additives stabilize DHA when the DHA is present in a dry mixture, and that DHA powder can be processed into a tablet or powder-filled capsule that exhibits excellent pharmaceutical stability when admixed with such additives. These additives include elemental iron, calcium ascorbate, silicon dioxide, calcium carbonate, magnesium chelate and copper chelate, and combinations thereof.

For example, it has been discovered that elemental iron can improve the stability of dry DHA by more than 75%, when other iron compounds such as ferrous fumarate decrease the stability of DHA by more than 200%. In like manner, it has been discovered that chelated copper can improve the stability of dry DHA by approximately 50% compared to DHA mixed with uncomplexed ascorbic acid. Silicon dioxide also has an impressive effect on the stability of DHA reducing the degradation of the molecule from 25% to just 4% when admixed together. With respect to magnesium, it has been discovered that chelated magnesium can improve the stability of dry DHA by more than 50%, when other magnesium compounds such as magnesium oxide decrease the stability of DHA. With respect to copper, it has been discovered that chelated copper can improve the stability of dry DHA by more than 75%, when other copper compounds such as cupric oxide decrease the stability of DHA by more than 200%.

Therefore, in one embodiment, the invention provides a nutritional supplement in the form of an orally administered tablet or powder-filled capsule comprising:
 a) dry docosahexaenoic acid (DHA) in an amount of from 100 to 300 mg; and
 b) an additive selected from elemental iron, calcium ascorbate, silicon dioxide, calcium carbonate, chelated magnesium, chelated copper and combinations thereof, in an amount sufficient to stabilize said DHA from oxidative degradation.

In another embodiment, the invention provides a method of stabilizing dry docosahexaenoic acid (DHA) comprising:
 a) providing said DHA in the form of a dry particulate, wherein said particulate further comprises one or more compression binders; and
 b) admixing said dry particulate with an additive selected from elemental iron, calcium ascorbate, chelated copper, chelated magnesium, silicon dioxide, calcium carbonate and combinations thereof, and one or more tablet excipients selected from lubricants, disintegrants and binders, to form an admixture.

In still another embodiment, the invention provides a nutritional supplement in the form of an orally administered tablet or powder filled capsule comprising:
 a) dry docosahexaenoic acid (DHA) in an amount of from 100 to 300 mg;
 b) elemental iron;
 c) copper as copper chelate;
 d) magnesium as magnesium chelate; and
 e) ascorbic acid as calcium ascorbate.

Yet another embodiment provides a nutritional supplement in the form of a tablet or a powder-filled capsule comprising:
 a) 50-60 mg of vitamin C as calcium ascorbate;
 b) 200-1000 IU of vitamin D3 (cholecalciferol);
 c) 10-20 IU of vitamin E (dl-alpha tocopheryl acetate);
 d) 10-30 mg of vitamin B5 (pyridoxine hydrochloride);
 e) 500-2000 mg of folic acid;
 f) 5-25 mcg of vitamin B 12 (cyanocobalamin);
 g) 50-200 mg of calcium (as calcium carbonate);
 h) 10-50 mg of iron (elemental);
 i) 25-60 mg of magnesium (as magnesium chelate); and
 j) 100-300 mg of DHA.

Additional embodiments and advantages of the invention will be set forth in part in the description which follows, and in part will be obvious from the description, or may be learned by practice of the invention. The embodiments and advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF INVENTION

The present invention may be understood more readily by reference to the following detailed description of preferred embodiments of the invention and the Examples included therein.

As noted above, the invention is premised on the discovery that DHA in the form of compressed oral tablets or powder filled capsules can be stabilized by the addition of various additives, including elemental iron, calcium ascorbate, silicon dioxide, calcium carbonate, chelated copper, chelated magnesium, and combinations thereof. The mechanism of stabilization is not completely understood, although it is hypothesized that the stabilization is due to a charge balance that the additive species contributes to the overall composition. To accomplish this function, it is generally preferred that the additive and DHA be intimately mixed and dispersed throughout the dosage form to maximize the chemical interaction between the two components.

Elemental iron, also known as carbonyl iron, is marketed commercially as Feronyl®. The material preferably is at least 98% pure iron, and loses no more than 10% of its weight on drying. In addition, 100% of the material is preferably 200 mesh or smaller. When reference is made in this document to "iron," it will be understood that elemental iron is intended.

DHA refers to docosahexaenoic acid, an omega-3 essential fatty acid with a 22-carbon chain and six cis double bonds The DHA can be derived from any appropriate source, including fish oils and algae extracts such a *Crypthecodinium cohnii* and another of the genus *Schizochytrium*, but of necessity it must be dry for it to be compressed into a solid unit such as a tablet or filled into a capsule. The term "dry" refers to a state wherein the DHA contains no more than 15, 10, 5 or 3% water by weight (i.e. exhibits no more than the foregoing weight percentages on drying).

The DHA used in the dosage forms of the present invention is typically supplied as a dry flowable composition such as a powder or granulate. For ease of reference herein, any dry flowable composition will be referred to simply as a "powder" or "particulate" composition. I.e., "powder" and "particulate" or "particle" are used interchangeably herein. Particulates may be prepared by numerous techniques that are well-known in the art, and may contain more than one component (i.e. composite particulates). Such methods include methods used commercially for processing fatty oils into food-grade materials, such as microencapsulation or drying. Such methods include, for example, spray-drying, spray-cooling, spray-chilling, air suspension coating, extrusion, centrifugal extrusion, freeze-drying, coacervation, rotational suspension separation, co-crystallization, liposome entrapment, interfacial polymerization, molecular inclusion, etc. Preferred drying methods include freeze drying and spray drying, as disclosed by K. Masters in SPRAY DRYING HANDBOOK, 5th edition, Longman Scientific Technical UK, 1991, the disclosure of which is hereby incorporated by reference. An excellent review of such techniques is given by Gharsallaoui et al. in FOOD RESEARCH INTERNATIONAL 40 (2007) 1107-1121.

A particularly suitable spray drying technique, reported by Lin et al. in JOURNAL OF FOOD SCIENCE, 60 (1995) 36-39 for the encapsulation of squid oil, uses wall materials of gelatin, sodium caseinate, and maltodextrin. The addition of lecithin and carboxymethyl cellulose was reported to improve encapsulating effectiveness and oxidative and thermal stabilities. The most effective formulation that showed the best thermal stability was (oil/gelatin/caseinate/maltodextrin/lecithin/carboxymethyl cellulose) of (30/20/20/20/4/1).

The DHA particles may be characterized by numerous physical and chemical criteria, including the percentage of DHA in the particle, the other ingredients of the particle, how DHA is distributed through the particle, loss on drying and particle size. The particulate must also be flowable, so that it may be accurately poured, processed and admixed in conventional mixing and tableting or capsule filling equipment. The DHA particles preferably comprise at least 20%, 30% 40%, or even 45% DHA based on the weight of the particle, but typically contain no more than 80%, 70%, 60% or 55% DHA. The remaining content of the particle includes materials present in the original source of fatty acids, and the ingredients used in the drying and particle forming process.

The DHA of the present invention is preferably highly concentrated in DHA, in the sense that it is substantially free of other long chain fatty acids such as eicosapentaenoic acid. Thus, in various embodiments the DHA particles, as well as the ultimate tablets and capsules manufactured from the particles, contain less than 30%, 20%, 10%, 5%, 2% or 1% polyunsaturated fatty acids (other than DHA) based on the weight of DHA. In alternative embodiments the DHA particles, as well as the ultimate tablets and capsules manufactured from the particles, contain less than 30%, 20%, 10%, 5%, 2% or 1% EPA based on the weight of DHA. For purposes of this invention, a polyunsaturated fatty acid is preferably defined to contain from 12 to 40 carbon atoms in its chain terminated by a carboxylic acid function, with at least 3 degrees of ethylenic unsaturation.

Carbohydrates such as starches, maltodextrins and corn syrup solids are usually used in microencapsulation of food ingredients, and are suitable for producing particles of the present invention. However, it will be understood that particle excipients that are based on these compounds have poor interfacial properties and must be chemically modified in order to improve their surface activity. In contrast, proteins have an amphiphilic character that offer physicochemical and functional properties required to encapsulate hydrophobic core materials. Of these, protein compounds such as sodium caseinate, soy protein isolate, and whey protein concentrates and isolates, can be expected to have good microencapsulating properties. Gums may also be used for both their film forming and emulsion stabilization properties. Among all gums, acacia gum, generally called gum arabic, stands out due to its excellent emulsification properties and thus may be used. In a preferred embodiment, the powder is made using a starch derivative, preferably a dextrin such as maltodextrin or cyclodextrin. In an even more preferred embodiment the powder is made using a dextrin and silicon as inactive excipients in the particle.

How DHA is distributed through the particle will ultimately be a function of the method by which the DHA is dried into particulate form. Thus, the morphology of the particles can be described as simple, multi-core, irregular, multi-wall, or matrix, as those terms are used and understood in the art, as described by Gharsallaoui et al. in FOOD RESEARCH INTERNATIONAL 40 (2007) 1107-1121. The stabilizing effects will be observed without regard to the particular morphology of the particle, given the intimate association among molecules created by the compression process when making tablets or filling process when making capsules.

The DHA particle size may range from 10-50 microns to 2-3 mm, depending on the method used to make the particle. In a preferred embodiment greater than 50% of the particles are able to pass through a 20 mesh screen.

The amounts of DHA and stabilizing additive in the dosage form can be stated on an absolute basis, as a percentage of the total weight of the dosage form, or in proportion to each other. It will be understood that any of these values can be selected and combined with any other of the values to define the compositions and methods of the present invention. Therefore, the amount of DHA in the tablet or capsule may range from 25 to 300 mg, from 100 to 300 mg, from 50 to 250 mg, from 100 to 250 mg, from 75 to 200 mg, or from 100 to 150 mg. The total percentage of DHA in the dosage form, based on the weight of the dosage form, is preferably greater than 10 or 20 wt. %, but preferably less than 50, 40 or 30 wt. %.

The amount of iron in the dosage form may range from 10 to 40 mg, from 12 to 35 mg, or from 15 to 30 mg. The total percentage of iron in the dosage form, based on the weight of the dosage form, is preferably greater than 1.5 or 3 wt. %, but preferably less than 8 or 6 wt. %.

The ratio of iron:DHA in the dosage form is not critical to the invention, and any amount of elemental iron will impart some degree of stability to the DHA. However, for practical commercial reasons the ratio of iron:DHA in the product preferably range from 1:20 to 1:1 or 1:2 (iron:DHA); 1:12 to 1:2 or 1:3 (iron:DHA); or from 1:8 to 1:3 or 1:4 (iron:DHA).

Other DHA stabilizing agents may also be incorporated into the dosage form, including copper chelate, magnesium chelate, calcium ascorbate, silicon dioxide, calcium carbonate and combinations thereof, in addition or alternative to the iron. A preferred type of magnesium chelate is a powder of magnesium chelated by one or more amino acids, wherein the elemental magnesium makes up about 20% of the entire powder. Specifications for such products typically allow for 20-30% magnesium to accommodate for manufacturing variations and product degradation.

The total amount of elemental magnesium contributed by the chelated magnesium is preferably from 5 to 200 mg, from 10 to 100 mg, and most preferably is from 10 to 50 mg. The total amount of chelated magnesium present in the dosage form, based on the weight of the entire complex, preferably ranges from 10 to 300 mg, 20 to 200 mg, or 30 to 100 mg. The total percentage of magnesium chelate in the dosage form, based on the weight of the dosage form, is preferably greater than 1.0, 2.0 or 5 wt. %, but preferably less than 30, 20, or 10 wt. %.

The ratio of magnesium:DHA in the dosage form is not critical to the invention, and any amount of chelated magnesium will impart some degree of stability to the DHA. However, for practical commercial reasons the ratio of magnesium:DHA in the product preferably ranges from 5:200-200:200 (magnesium:DHA); 10:200-100:200 (magnesium:DHA); or 10:200-50:200 (magnesium:DHA). These ratios are based on the elemental magnesium contributed by the chelate. Additional ratios and ranges can be expressed based on the weight of the chelate, by assuming that the magnesium is present as a 20 or 30% chelate.

A preferred type of copper chelate is a granular powder of copper chelated by one or more amino acids, wherein the elemental copper makes up about 20% of the entire powder. Specifications for such products typically allow for 20-25% copper to accommodate for manufacturing variations and product degradation.

The total amount of elemental copper contributed by the chelated copper is preferably from 1 to 5 mg, from 1 to 3 mg, and most preferably is from 1 to 2 mg. The total amount of chelated copper present in the dosage form, based on the weight of the entire complex, preferably ranges from 5 to 50 mg, 7.5 to 30 mg, or 10 to 20 mg. The total percentage of copper chelate in the dosage form, based on the weight of the dosage form, is preferably greater than 0.5, 1.0, 1.5, 2.0 or 3 wt. %, but preferably less than 10, 8, 6 or 4 wt. %.

The ratio of copper:DHA in the dosage form is not critical to the invention, and any amount of chelated copper will impart some degree of stability to the DHA. However, for practical commercial reasons the ratio of copper:DHA in the product preferably ranges from 1:300 to 1:20 (copper:DHA); 1:300 to 1:50 (copper:DHA); or 1:300 to 1:100 (copper:DHA). These ratios are based on the elemental copper contributed by the chelate. Additional ratios and ranges can be expressed based on the weight of the chelate, by assuming that the copper is present as a 10% or 20% chelate.

A preferred type of calcium carbonate is a powder form that contains from 87.4 to 95% by weight calcium carbonate, and 35 to 38.1% by weight calcium. The particles preferably lose no more than 10% by weight on drying. The particles are preferably defined by a size range, wherein 100% of the powder passes through a mesh 16 screen, not more than 75% of the powder passes through a 60 mesh screen, and not more than 15% of the powder passes through a 200 mesh screen.

Alternatives amounts of these ingredients in the tablets or capsules, expressed on an absolute basis, and as a percentage of the total weight of the tablet or capsule, are given below:

| | |
|---|---|
| Calcium ascorbate (based on weight and percentage of ascorbic acid) | 10-150 mg; 20-100 mg; 40-80 mg; 2-20%; 5-15% |
| Copper chelate (based on weight and percentage of elemental copper) | 1-5 mg; 1-3 mg; 1-2 mg; from 0.5, 1.0, 1.5, 2.0 or 3 wt. % to 10, 8, 6 or 4 wt. %. |
| Elemental Iron | 5-50 mg; 10-40 mg; 15-30 mg; 0.5-10%; 1-8%; 2-6% |
| Magnesium chelate (based on weight and percentage of elemental magnesium) | 5-200 mg; 10-100 mg; 10-50 mg; 0.5-10%; 1.0-5% |
| Calcium carbonate | 100-400 mg; 200-350 mg; 20-70%; 30-60% |
| Silicon dioxide | 50-300 mg; 100-200 mg; 2-15%; 3-10%; 5-30%; 5-20% |

Once again, the ratio of DHA to any of these stabilizing ingredients in the dosage form is not critical to the invention, and any amount of these stabilizing ingredients will impart some degree of stability to the DHA. However, for practical commercial reasons the ratio of DHA to these stabilizing agents in the product preferably fall within one of the following ranges:

| | |
|---|---|
| Calcium ascorbate:DHA (based on weight of ascorbic acid) | 10:200-150:200; 20:200-100:200; 40:200-80:200 |
| Copper chelate:DHA (based on weight of elemental copper) | 1:300-1:20; 1:300-1:50; 1:300-1:100 |
| Iron:DHA | 5:200 to 50:200; 10:200-40:200; 15:200-30:200 |
| Magnesium chelate:DHA (based on weight of elemental magnesium) | 5:200-200:200; 10:200-100:200; 10:200-50:200 |
| Calcium carbonate:DHA | 1:1 to 8:1; 2:1 to 5:1; 1:4 to 4:1 |
| Silicon dioxide:DHA | 1:1 to 1:4; 1:1.5 to 1:3 |

A particularly suitable mix of active ingredients in the dosage form can be defined to comprise based on the formulation in Tables A, B and C, it being understood that the ingredients can be combined in any of the amounts or ranges of amounts stated in the table, and that other active ingredients can also be included with the formulation:

TABLE A

| Vitamins | |
|---|---|
| C (as calcium ascorbate) | 50-60 mg |
| D3 (cholecalciferol) | 200 IU |
| E (dl-alpha tocopheryl acetate) | 15 IU |
| B1 (thiamine mononitrate) | 1-1.5 mg |
| B2 (riboflavin) | 1.7-2 mg |
| B3 (Niacinamide) | 10 mg |
| B6 (pyridoxine hydrochloride) | 12.5-15 mg |
| Folic acid | 500 mcg |
| B12 (cyanocobalamin) | 25 mcg |
| Biotin | 0, 150 mcg |
| Minerals | |
| Calcium (as calcium carbonate) | 75 mg |
| Iron (Elemental) | 25 mg. |
| Iodine (potassium iodide) | 0-75 mcg |
| Magnesium (as magnesium chelate) | 25 mg |
| Zinc (zinc oxide) | 7.5-12.5 mg |
| Copper (as copper chelate)) | 1 mg |
| Also contains | |
| DHA omega-3 fatty acids | 125 mg |

TABLE B

| Vitamins | |
|---|---|
| C (as calcium ascorbate) | 50-60 mg |
| D3 (cholecalciferol) | 200-1000 IU |
| E (dl-alpha tocopheryl acetate) | 10-20 IU |
| B6 (pyridoxine hydrochloride) | 10-30 mg |
| Folic acid | 500-2,000 mcg |
| B12 (cyanocobalamin) | 5-25 mcg |
| Minerals | |
| Calcium (as calcium carbonate) | 50-200 mg |
| Iron (Elemental) | 10-50 mg |
| Magnesium (as magnesium chelate) | 25-60 mg |
| Also contains | |
| DHA omega-3 fatty acids | 100-300 mg |

TABLE C

| Vitamins | |
|---|---|
| C (optionally as calcium ascorbate) | 50-60 mg |
| D3 (cholecalciferol) | 200-1000 IU |
| E (dl-alpha tocopheryl acetate) | 10-20 IU |
| B6 (pyridoxine hydrochloride) | 10-30 mg |
| Folic acid | 500-2,000 mcg |
| B12 (cyanocobalamin) | 5-25 mcg |
| Minerals | |
| Calcium (optionally as calcium carbonate) | 50-200 mg |
| Iron (optionally as elemental iron) | 10-50 mg |
| Magnesium (optionally as magnesium chelate) | 25-60 mg |
| Also contains | |
| DHA omega-3 fatty acids | 100-300 mg |

Tablet Manufacture

The tablets of the invention may be produced by compression or compaction of a formulation containing the fatty acid compound and/or particulates thereof and certain excipients, typically selected to aid in the processing and to improve the properties of the tablet. The tablets of the invention may be coated or uncoated and can be made from powdered, crystalline materials. Tablets may be plain, film or sugar coated, bisected, embossed, layered, or sustained release. Any film coating preferably comprise of a physiologically acceptable water-soluble organic polymer. The tablets can be made in a variety of sizes, shapes and colors.

Excipients which may be present include diluents, binders, disintegrants, lubricants, glidants and in many cases, colorants. These excipients may derive from the DHA particles that are used in the tablet manufacturing process, or they may be added separately. For ease of reference, these excipients will be distinguished as "DHA particle excipients" and "tablet excipients." When reference is given simply to "excipients," it will be understood that both sources of excipients are intended.

The excipients used are classified according to the function they perform. For example, a glidant may be used to improve the flow of powder blend in the hopper and into the tablet die. Lubricants are typically added to prevent the tableting materials from sticking to punches, minimize friction during tablet compression, and allow for removal of the compressed tablet from the die. Such lubricants are commonly included in the final tablet mix in amounts usually less than 1% by weight. The most commonly used lubricants are magnesium stearate, stearic acid, hydrogenated oil, and sodium stearyl fumarate.

Tablets often contain diluents, such as lactose, which are added to increase the bulk weight of the blend resulting in a practical size for compression. Typical diluents include for example dicalcium phosphate, calcium sulphate, lactose, cellulose (esp. microcrystalline cellulose), kaolin, mannitol, sodium chloride, dry starch and other sugars. This is often necessary where the dose of the drug is relatively small. Given the relative load of DHA particles in the tablets of the present invention, the use of such diluents is generally disfavored and minimized. It is preferred if the total weight of tablet excipients in a tablet of the invention is no more than 20 wt % of that tablet, preferably less than 15 wt % of the tablet, especially less than 10 wt % of the tablet.

Binders are agents which impart cohesive qualities to the powdered material. Commonly used binders include starch, gelatin, sugars such as sucrose, glucose, dextrose, and lactose, natural and synthetic gums, carboxymethylcellulose, methylcellulose, polyvinylpyrrolidone, ethylcellulose and waxes. Disintegrants are often included to ensure that the tablet has an acceptable rate of disintegration. Typical disintegrants include starch derivatives, crospovidone, croscaramelose and salts of carboxymethylcellulose. Some binders, such as starch and cellulose, are also excellent disintegrants.

Other desirable characteristics of excipients include high compressibility to allow strong tablets to be made at low compression forces, good flow properties that can improve the flow of other excipients in the formula and cohesiveness (to prevent tablet from crumbling during processing, shipping and handling). The skilled artisan knows the type of excipients appropriate for tablet formulation.

The three main processes for making compressed tablets are wet granulation, direct compression, and dry granulation (slugging or roller compaction). Dry granulation consists of blending, slugging the ingredients, dry screening, lubrication, and compression. The wet granulation method is used to convert a powder mixture into granules having suitable flow and cohesive properties for tableting. The procedure consists of mixing the powders in a suitable blender followed by adding the granulating solution under shear to the mixed powders to obtain a granulation. The damp mass is then screened through a suitable screen and dried by tray drying or fluidized bed drying. Alternately, the wet mass may be dried and passed through a mill. The overall process includes: weighing, dry powder blending, wet granulating, drying, milling, blending lubrication and compression.

While all three methods can be used to form the tablets of the invention, it is preferred if direct compression is employed. Direct compression is a relatively quick process where the powdered materials are compressed directly without changing the physical and chemical properties of the active principals. The fatty acid compound, direct compression excipients and any other auxiliary substances, such as a glidant and lubricant are blended, e.g. in a twin shell blender or similar low shear apparatus before being compressed into tablets. The advantages of direct compression include uniformity of blend, few manufacturing steps involved, (i.e. the overall process involves weighing of powders, blending and compression, hence less cost), elimination of heat and moisture, prime particle dissociation, and physical stability.

The size of the tablets, according to the present invention can vary. The tablet diameter can vary from 6 mm to 20 mm, preferably 8 to 14 mm. The tablet weight can vary from 100 mg to 3 grams. The most preferred tablets have tablet weights between 200 mg and 2 grams with a mean diameter from 8 to 12 mm. When caplets are used, the mean diameter will refer to the average of the length and width of the tablet.

Definitions and Use of Terms

As used in this specification and in the claims which follow, the singular forms "a," "an" and "the" include plural referents unless the context clearly dictates otherwise. Thus, for example, reference to "an ingredient" includes mixtures of ingredients, reference to "an active pharmaceutical agent" includes more than one active pharmaceutical agent, and the like.

When the weight of DHA or other active ingredient is given herein, it will be understood that the weight refers to the actual DHA present in the composition, as opposed to the weight of any particles in which the DHA is supplied. It will also be understood that the given weight accommodates such variability as is customary in the art of pharmaceutical sciences and dietary supplements. Just as a tablet may contain an amount of active ingredient that differs from the amount stated on the tablet's label on account of manufacturing imprecision and product degradation, a weight specified in the claims accommodates comparable variability.

When an elemental ingredient weight is given, and the ingredient is identified as being present in a particular form, it will be understood that the recited weight refers to the weight of the element. Thus, for example, if a tablet contains 50 mg of copper as copper oxide, it would contain 50 mg. of elemental copper, and approximately 63 mg. of copper oxide.

In one embodiment, the DHA particles of the present invention are microencapsulated. Microencapsulation is defined as a process in which tiny particles or droplets are surrounded by a coating, or embedded in a homogeneous or heterogeneous matrix. Microencapsulation can, but need not, provide a physical barrier between the core compound and the other components of the product. More especially, in the food field, microencapsulation is a technique by which liquid droplets, solid particles or gas compounds are entrapped into thin films of a food grade microencapsulating agent.

As used herein, an ambient environment refers to the environment immediately surrounding an element or process, typically a gaseous environment, with which the element or process is in contact and communication.

Shelf stability, for purposes of this invention, is measured by storing the dosage form in its packaging at 40° C., at a relative humidity of 75% (i.e. accelerated conditions), or under ambient conditions, for three, six, twelve, eighteen, twenty-four, thirty or thirty-six months. A stable formulation is one in which no more than about 50, 40, 30, 20 or 10 wt. % of the DHA in the dosage form degrades during any one of these time periods. The additives of the present invention are preferably able to reduce the degradation of DHA, compared to compositions without the additive, by more than 1%, 3%, 5%, 10%, or 25% when tested under accelerated conditions for three months.

When ranges are given by specifying the lower end of a range separately from the upper end of the range, it will be understood that the range can be defined by selectively combining any one of the lower end variables with any one of the upper end variables that is mathematically possible.

When used herein the term "about" or "ca." will compensate for variability allowed for in the dietary supplement industry and inherent in dietary supplements, such as differences in product strength due to manufacturing variation and time-induced product degradation. The term allows for any variation which in the practice of dietary supplements would allow the product being evaluated to be considered equivalent to the recited strength of a claimed product.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric Example 1

Analytical Methods

The following is a description of a method suitable for the determination of fatty acids in the DHA raw material used in the present invention, and the tablets produced using the methods described in this document. The chromatography can be performed by use of Agilent 6890N Gas Chromatographer Reagents and Materials: 50 ml test tube; Methanol (MeOH); Hexane; Isooctane (IO) (Sigma); 450 ml beaker; Sodium hydroxide; BF3-12% in methanol (Sigma); Sodium chloride.

Solution Preparation: 0.5N NaOH; Dissolve 2.0 g NaOH in methanol and make to 100 ml with methanol. Saturated NaCl solution: Dissolve 36 g NaCl in 100 ml of distilled water.

Extraction of Oil from Powder: Weigh about 10 g of oil powder in a beaker and record the weight (Wa.). Add 100 ml of distilled water and 100 ml hexane. Stir the solution for 5 min and divide the mixed solution into 6 of 50 ml centrifuge tubes. Centrifuge 5 min at 3000 rpm and transfer hexane layer to a separate funnel. Add 10 ml of hexane to each centrifuge tube and vortex for 1 min. Centrifuge 5 min at 3000 rpm and transfer hexane layer to a separate funnel. Add 10 ml of hexane to each centrifuge tube and vortex for 1 min. Centrifuge again and combine hexane phase. Add 10 ml of distilled water to hexane to phase and shake and save the top hexane phase. Use 10 ml of saturated sodium chloride to wash hexane phase. Transfer the hexane phase to a beaker with sodium sulfate inside. Filter the solution to a weighted beaker (Wb). Evaporate the solvent at water bath and cool to room temperature. Weigh the beaker with oil inside (Wc) and calculate Fat content (see equation 1).

GC Sample Preparation: Weigh about 50 mg of oil sample and add 1.5 ml of 0.5 N NaOH solution and blanket with nitrogen, cap tightly, mix and heat at 100 C water bath for 5 min. Cool to room temperature, add 2 ml BF3/methanol reagent, blanket with nitrogen, vortex and heat at 100 C for 30 min. Cool to 30-40 C, add 2 ml of IO solution, blanket with nitrogen and vortex for 30 sec while still warm. Add 5 ml of Sat NaCl and agitate thoroughly. Cool to room temperature. After isooctane layer separates from water layer, transfer IO layer to a GC sample vial. Inject 1 ml of the sample to GC.

GC Test Conditions: Column: J&W GC Column (bought from Agilent). DB-5 30 m*0.25 mm*0.25 um; Inject 1 ul at 250 C; Split at 250 C at 20:1; Detector, 270 C; Oven temperature profile: Initial temperature, 150 C and hold 0 min; Program rate, 4 C/min; Final temperature. 250 C and hold 0 min.

Calculation: Total fat content (%)=((Wc−Wb)/Wa)*100; Percentage of DHA in oil=Area of DHA/(total area−solvent area)*100.

All stability studies were undertaken in accordance with methods described in the United States Pharmacopoeia (2008). Samples were stored at room temperature under ambient conditions, and under accelerated conditions at 40° C. in a controlled humidity chamber at 75% relative humidity.

Example 2

Compatibility Studies

50:50 mixtures by weights of a dry DHA powder and various tableting excipients were made to evaluate their compatibility. The ingredients were supplied as dry powders, thoroughly mixed, and compressed into tablet dies at a compression pressure of approximately 5 tons. The mixtures tested, and their loss of potency after three months of storage under accelerated conditions, is reported in Table 1:

TABLE 1

| Product Raw material mix with RW2147[a] | Code | potency theoretical | potency actual | % loss |
|---|---|---|---|---|
| Compression RW2147 Pure | 3056 | 1000 mg | 750 | 25 |
| Dicalcium phosphate Dihydrate 50:50 | 3054 | 250 mg | 40 | 74 |
| Calcium Carbonate | | | | 26 |
| Calcium Ascorbate 50:50 | 3066 | 250 mg | 194 | 39 |
| Vitamin C 97% DC 50:50 | 3055 | 250 mg | 85 | 64 |
| Silicon Dioxide 50:50 | 3057 | 250 mg | 240 | 4 |
| Ferrous Fumarate USP 50:50 | 3058 | 250 mg | 28 | 89 |
| Ferronyl Iron 50:50 | 3059 | 250 mg | 235 | 6 |
| Magnesium Oxide Heavy gran. 50:50 | 3060 | 250 mg | 175 | 30 |
| Magnesium Chelate 50:50 | 3062 | 250 mg | 225 | 10 |
| Cupric Oxide 50:50 | 3061 | 250 mg | 174 | 30 |
| Copper Chelate 50:50 | 3063 | 250 mg | 240 | 4 |
| Zinc Sulfate 50:50 | 3064 | 250 mg | 172 | 31 |
| Zinc Chelate 50:50 | 3065 | 250 mg | 192 | 40 |

[a]RW 2147 refers to O2P DHA 70 EE Oil Powder (NG), marketed by Sun Naturals, Inc., Oviedo, Florida. The product meets the following specifications: EPA ≥ 26 mg/g; DPA ≥ 16 mg/g; DHA ≥ 470 mg/g; total omega-3 fatty acids ≥ 500 mg/g; particle size > 50% thru 20 mesh; bulk density 0.30-0.60 g/ml; moisture < 2%. The powder contains DHA 70 EE Oil, maltodextrin and silicon. DHA 70 EE Oil contains: EPA ≥ 38 mg/g; DPA ≥ 23 mg/g; DHA ≥ 670 mg/g; total omega-3 fatty acids ≥ 720 mg/g.

Example 3

Formulation Stability Studies

Various finished formulations were also compressed into tablets and tested for their stability under accelerated and room temperature conditions. Tables 2-5 list the ingredients of the formulations tested. Table 6 lists the results of the stability testing under accelerated stability conditions.

TABLE 2

(53987m) (unstable)

| ING # | mg/unit | total mg | INGREDIENT DESCRIPTION |
|---|---|---|---|
| 1 | 2000 | 4 | Vitamin A Acetate 500 m iu/g (1) |
| 2 | 500 | 3.012048 | Beta Carotene 10% (1) |
| 3 | 0.02 | 2.2 | Vitamin K1 1% (1) |
| 4 | 4.5 | 5.05102 | Vitamin B1 (Thiamine) Mono (6) |
| 3 | 3.4 | 3.936842 | Vitamin B2 (Riboflavin) (7) |
| 4 | 6 | 8.25 | Vitamin B6 (Pyridoxine) (5) |
| 5 | 0.025 | 2.75 | Vitamin B12 (Cyanocobalamin) 1% (1) |
| 6 | 0.4 | 0.412371 | Folic Acid 97% (1) |
| 7 | 400 | 4 | Vitamin D3 (100,000 IU/g) (1) |
| 8 | 120 | 123.7113 | Ascorbic Acid 97% Cellulose (1) |
| 9 | 33 | 28.39931 | Vitamin E Acetate 50% (1) |
| 10 | 20 | 23.15789 | Vitamin B3 (Niacinamide) (5) |
| 11 | 0.03 | 3 | Biotin 1% (8) |
| 12 | 15 | 16.5 | Vitamin B5 (D-Calcium Pantothenate) (7) |
| 13 | 2 | 2.5 | Copper Oxide 80% |
| 14 | 100 | 166.6667 | Magnesium Oxide Gran. 60% (1) |
| 15 | 22.5 | 64.28571 | Zinc Sulfate 35% (1) |
| 16 | 0.105 | 21 | Selenomethionine (5000 mcg/g) (1) |
| 17 | 4 | 12.90323 | Manganese Sulfate 31.4% (1) |
| 18 | 0.18 | 1.090909 | Chromium Polynicotinate 16.5% |
| 19 | 40 | 76.92308 | Potassium Chloride 50-53% Granular (1) |
| 20 | 0.15 | 0.197368 | Potassium Iodine 76.5% |
| 21 | 0.09 | 45 | Molybdenum Chelate 0.2% (1) |
| 22 | 17 | 40.8 | DHA 50% powder (RW 2147) |
| 24 | 0.5 | 5.5 | Asta Zanthin 10% |
| 25 | 10 | 11 | L-Glutathione (1) |
| 26 | 120 | 133.3333 | Di-Tab (Di Calcium Phosphate) (1) |
| 27 | 150 | 150 | Micro Crystalline Cellulose (Tabulose) |
| 28 | 12 | 12 | Stearic Acid (1) |
| 29 | 10 | 10 | Silicon Dioxide (Flo-gard) |
| 30 | 11 | 11 | Croscamellose Sodium (Solutab-Blanver, Accelerate-Stauber) (2) |
| 31 | 11 | 11 | Magnesium Stearate (Vegetable Grade) (1) |

TABLE 3

(53309m.b.1) (unstable)

| ING # | mg/unit | total mg | INGREDIENT DESCRIPTION |
|---|---|---|---|
| 1 | 2100 | 2.1 | Vitamin A Acetate 500 m iu/g (1) |
| 2 | 2 | 1.122449 | Vitamin B1 (Thiamine) Mono (6) |
| 3 | 3.4 | 1.968421 | Vitamin B2 (Riboflavin) (7) |
| 4 | 10 | 6.875 | Vitamin B6 (Pyridoxine) (5) |
| 5 | 0.015 | 0.825 | Vitamin B12 (Cyanocobalamin) 1% (1) |
| 6 | 0.8 | 0.412371 | Folic Acid 97% (1) |
| 7 | 315 | 1.575 | Vitamin D3 (100,000 IU/g) (1) |
| 8 | 120 | 69.76744 | Calcium Ascorbate 6-83% (1) |
| 9 | 20 | 8.605852 | Vitamin E 1185SI (d-alpha tocopheryl) (1) |
| 10 | 10 | 5.789474 | Vitamin B3 (Niacinamide) (5) |
| 11 | 1 | 3.846154 | Copper Gluconate 13% |
| 12 | 15 | 37.5 | Magnesium Chelate 20% (1) |
| 13 | 10 | 25 | Zinc Chelate (20%) (1) |
| 14 | 28 | 14.14141 | Iron Ferronyl 98% |
| 15 | 400 | 666.6667 | DHA 50% powder (RW 2147) |
| 16 | 350 | 486.1111 | Calcium Carbonate Hvy Usp Granular 38% (5) |
| 17 | 200 | 100 | Micro Crystalline Cellulose (Tabulose) |
| 18 | 120 | 60 | Stearic Acid (1) |
| 19 | 50 | 25 | Silicon Dioxide (Flo-gard) |
| 20 | 34 | 17 | Croscamellose Sodium (Solutab-Blanver, Accelerate-Stauber) (2) |
| 21 | 34 | 17 | Magnesium Stearate (Vegetable Grade) (1) |

TABLE 4

(53309m.b) (stable)

| ING # | mg/unit | total mg | INGREDIENT DESCRIPTION |
|---|---|---|---|
| 1 | 2100 | 2.1 | Vitamin A Acetate 500 m iu/g (1) |
| 2 | 2 | 1.122449 | Vitamin B1 (Thiamine) Mono (6) |
| 3 | 3.4 | 1.968421 | Vitamin B2 (Riboflavin) (7) |
| 4 | 10 | 6.875 | Vitamin B6 (Pyridoxine) (5) |
| 5 | 0.015 | 0.825 | Vitamin B12 (Cyanocobalamin) 1% (1) |
| 6 | 0.8 | 0.412371 | Folic Acid 97% (1) |
| 7 | 315 | 1.575 | Vitamin D3 (100,000 IU/g) (1) |
| 8 | 120 | 69.76744 | Calcium Ascorbate 6-83% (1) |
| 9 | 20 | 8.605852 | Vitamin E 1185SI (d-alpha tocopheryl) (1) |
| 10 | 10 | 5.789474 | Vitamin B3 (Niacinamide) (5) |
| 11 | 1 | 3.846154 | Copper Gluconate 13% |
| 12 | 15 | 37.5 | Magnesium Chelate 20% (1) |
| 13 | 10 | 25 | Zinc Chelate (20%) (1) |
| 14 | 28 | 14.14141 | Iron Ferronyl 98% |
| 15 | 200 | 220 | DHA 50% powder (RW 2147) |
| 16 | 300 | 652.1739 | Calcium Carbonate Hvy Usp Granular 38% (5) |
| 17 | 500 | 250 | Micro Crystalline Cellulose (Tabulose) |
| 18 | 30 | 15 | Stearic Acid (1) |
| 19 | 160 | 80 | Silicon Dioxide (Flo-gard) |
| 20 | 45 | 22.5 | Croscamellose Sodium (Solutab-Blanver, Accelerate-Stauber) (2) |
| 21 | 26 | 13 | Magnesium Stearate (Vegetable Grade) (1) |

TABLE 5

(53987m.a) (unstable)

| ING # | mg/unit | total mg | INGREDIENT DESCRIPTION |
|---|---|---|---|
| 1 | 2000 | 4 | Vitamin A Acetate 500 m iu/g (1) |
| 2 | 500 | 3.012048 | Beta Carotene 10% (1) |
| 3 | 0.02 | 2.2 | Vitamin K1 1% (1) |
| 4 | 4.5 | 5.05102 | Vitamin B1 (Thiamine) Mono (6) |
| 3 | 3.4 | 3.936842 | Vitamin B2 (Riboflavin) (7) |
| 4 | 6 | 8.25 | Vitamin B6 (Pyridoxine) (5) |
| 5 | 0.025 | 2.75 | Vitamin B12 (Cyanocobalamin) 1% (1) |
| 6 | 0.4 | 0.412371 | Folic Acid 97% (1) |
| 7 | 400 | 4 | Vitamin D3 (100,000 IU/g) (1) |
| 8 | 120 | 139.5349 | Calcium Ascorbate 6-83% (1) |
| 9 | 33 | 28.39931 | Vitamin E Acetate 50% (1) |
| 10 | 20 | 23.15789 | Vitamin B3 (Niacinamide) (5) |
| 11 | 0.03 | 3 | Biotin 1% (8) |
| 12 | 15 | 16.5 | Vitamin B5 (D-Calcium Pantothenate) (7) |
| 13 | 2 | 10 | Copper Chelate 20% (1) |
| 14 | 100 | 500 | Magnesium Chelate 20% (1) |
| 15 | 22.5 | 112.5 | Zinc Chelate (20%) (1) |
| 16 | 0.105 | 21 | Selenomethionine (5000 mcg/g) (1) |
| 17 | 4 | 12.90323 | Manganese Sulfate 31.4% (1) |
| 18 | 0.18 | 1.090909 | Chromium Polynicotinate 16.5% |
| 19 | 40 | 76.92308 | Potassium Chloride 50-53% Granular (1) |
| 20 | 0.15 | 0.197368 | Potassium Iodine 76.5% |
| 21 | 0.09 | 45 | Molybdenum Chelate 0.2% (1) |
| 22 | 17 | 40.8 | DHA 50% powder (RW 2147) |
| 24 | 0.5 | 5.5 | Asta Zanthin 10% |
| 25 | 10 | 11 | L-Glutathione (1) |
| 26 | 120 | 133.3333 | Di-Tab (Di Calcium Phosphate) (1) |
| 27 | 150 | 150 | Micro Crystalline Cellulose (Tabulose) |
| 28 | 12 | 12 | Stearic Acid (1) |
| 29 | 10 | 10 | Silicon Dioxide (Flo-gard) |
| 30 | 11 | 11 | Croscarmellose Sodium (Solutab-Blanver, Accelerate-Stauber) (2) |
| 31 | 11 | 11 | Magnesium Stearate (Vegetable Grade) (1) |

TABLE 6

(stability results)

| FORMULATION | Code | potency theoretical | potency actual | % potency actual |
|---|---|---|---|---|
| DHA prenatal | 53309m.b | 200 | 209 | 104.5 |
| DHA prenatal final formula 200 mg | 53309m.b | 200 | 250 | 125 |
| DHA prenatal at 1 mo. AC | 53309m.b | 200 | 220 | 110 |
| DHA prenatal at 2 mo. AC | 53309m.b | 200 | 210 | 105 |
| DHA prenatal at 3 mo. AC | 53309m.b | 200 | 190 | 95 |
| DHA prenatal at 3 mo. RT | 53309m.b | 200 | 205 | 102.5 |
| DHA womens at 1 mo. AC | 53987m | 17 | 0.8 | 5 |
| DHA womens at 1 m. AC | 53987m.a | 17 | 11 | 65 |
| DHA prenatal at 1 mo. AC | 53309m.b.1 | 400 | 418 | 104.5 |
| DHA prenatal at 1 mo. AC | 53309m.b.1 | 400 | 320 | 80 |

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A nutritional supplement in the form of an orally administered tablet or powder filled capsule comprising:
    a) dry docosahexaenoic acid (DHA) in an amount of from 100 to 300 mg;
    b) elemental iron in an amount of from 10 to 40 mg;
    c) 0.5-2.0 mg of copper as copper chelate;
    d) 0.5-2.0 mg of magnesium as magnesium chelate; and
    e) 20-100 mg of ascorbic acid as calcium ascorbate.

2. The nutritional supplement of claim 1, further comprising chelated zinc.

3. A nutritional supplement in the form of an orally administered tablet or powder filled capsule comprising:
    a) dry docosahexaenoic acid (DHA) in an amount of from 100 to 300 mg;
    b) elemental iron in an amount of from 10 to 40 mg;
    c) 10-50 mg of magnesium as magnesium chelate; and
    d) 20-100 mg of ascorbic acid as calcium ascorbate.

4. The nutritional supplement of claim 3 further comprising zinc chelate and copper chelate.

5. The nutritional supplement of claim 1 in the form of a tablet.

6. The nutritional supplement of claim 3 in the form of a tablet.

* * * * *